United States Patent [19]

Anderson

[11] Patent Number: 5,713,880
[45] Date of Patent: Feb. 3, 1998

[54] EXTERNAL MALE CATHETER

[75] Inventor: Verne M. Anderson, Chicago, Ill.

[73] Assignee: Medpoint Corporation, Chicago, Ill.

[21] Appl. No.: 626,353

[22] Filed: Apr. 2, 1996

[51] Int. Cl.[6] ............................................. A61F 5/44
[52] U.S. Cl. .................................. 604/349; 604/352
[58] Field of Search .............................. 604/349–352

[56] References Cited

U.S. PATENT DOCUMENTS

| | | |
|---|---|---|
| D. 253,009 | 9/1979 | Okamoto . |
| D. 254,808 | 4/1980 | Meldahl . |
| 1,105,488 | 7/1914 | Clare ................................. 604/352 |
| 2,348,773 | 5/1944 | Wyman . |
| 2,358,440 | 9/1944 | Bowman . |
| 2,577,345 | 12/1951 | McEwen . |
| 2,604,092 | 7/1952 | Brown et al. . |
| 2,940,450 | 6/1960 | Witt et al. . |
| 3,394,703 | 7/1968 | Orgel . |
| 3,403,682 | 10/1968 | McDonell . |
| 3,421,507 | 1/1969 | Gresham . |
| 3,511,241 | 5/1970 | Lee . |
| 3,520,305 | 7/1970 | Davis . |
| 3,608,552 | 9/1971 | Broerman ............................. 604/352 |
| 3,661,156 | 5/1972 | McLaughlin . |
| 3,742,953 | 7/1973 | Lee . |
| 3,863,638 | 2/1975 | Rogers, III et al. . |
| 4,232,675 | 11/1980 | Meldahl . |
| 4,475,909 | 10/1984 | Eisenberg . |
| 4,540,409 | 9/1985 | Nystrom et al. . |
| 4,588,397 | 5/1986 | Giacalone . |
| 4,626,250 | 12/1986 | Schneider . |
| 4,713,066 | 12/1987 | Komis . |
| 4,713,067 | 12/1987 | Rothenberg et al. . |
| 4,759,753 | 7/1988 | Schneider et al. . |
| 4,784,655 | 11/1988 | Campion et al. . |
| 4,790,834 | 12/1988 | Austin . |
| 4,794,920 | 1/1989 | Robichaud . |
| 4,798,600 | 1/1989 | Meadows . |
| 4,840,625 | 6/1989 | Bell . |
| 4,846,816 | 7/1989 | Manfredi . |
| 4,867,176 | 9/1989 | Lash . |
| 4,869,723 | 9/1989 | Harmon . |
| 4,872,464 | 10/1989 | Loeb et al. . |
| 4,966,166 | 10/1990 | Leffler . |
| 5,069,228 | 12/1991 | Sorkin . |
| 5,318,042 | 6/1994 | Gray . |
| 5,398,699 | 3/1995 | Fergus . |
| 5,419,341 | 5/1995 | Galasso . |

FOREIGN PATENT DOCUMENTS

| | | |
|---|---|---|
| 1498634 | 10/1967 | France . |
| 1591685 | 6/1970 | France . |
| 2083122 | 12/1971 | France . |

*Primary Examiner*—Robert A. Clarke
*Attorney, Agent, or Firm*—Hill, Steadman & Simpson

[57] ABSTRACT

An external male catheter has a drain tube connection end for connection to a drain tube or collection tube that leads to a collection bag. The drain tube connection end is connected to a larger tubular portion, the other end of which is connected to a reduced diameter central portion. The central portion is tubular as well and has its other end connected to a cuff portion of a diameter generally the same as that of the larger tubular portion. An embodiment without the cuff is provided, as is an embodiment with the cuff on a tubular sheath of generally constant diameter. An applicator for the external male urinary catheter includes a pivotally connected handle for parting a pair of roll engaging arcs which open the catheter for putting on the wearer.

2 Claims, 4 Drawing Sheets

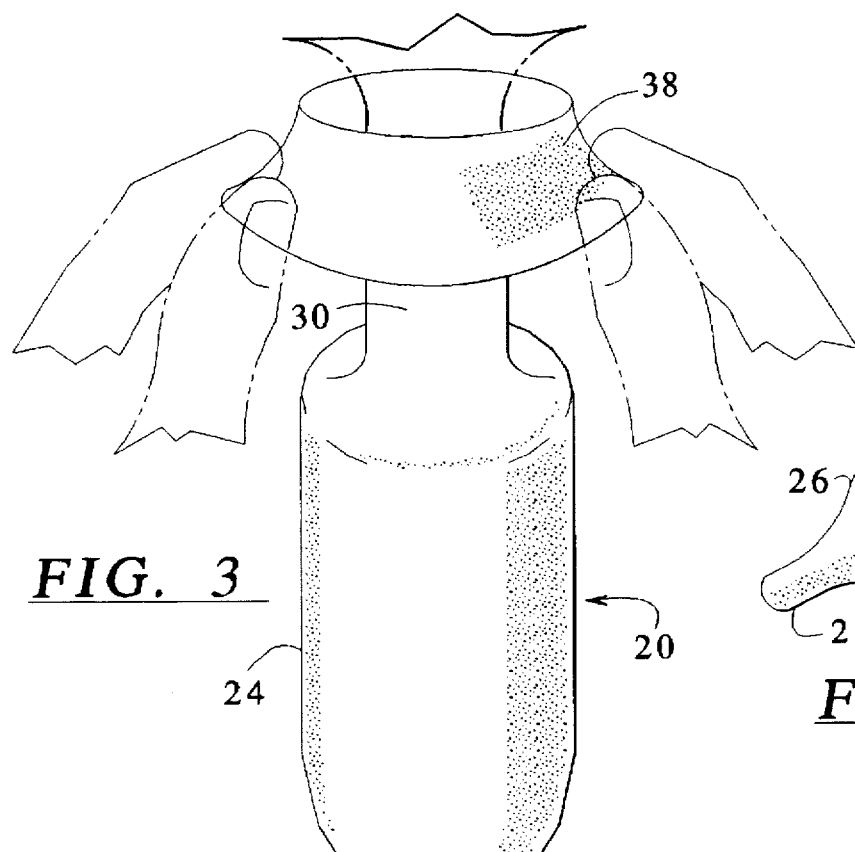
FIG. 3
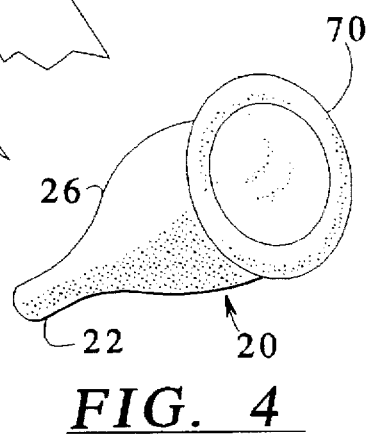
FIG. 4
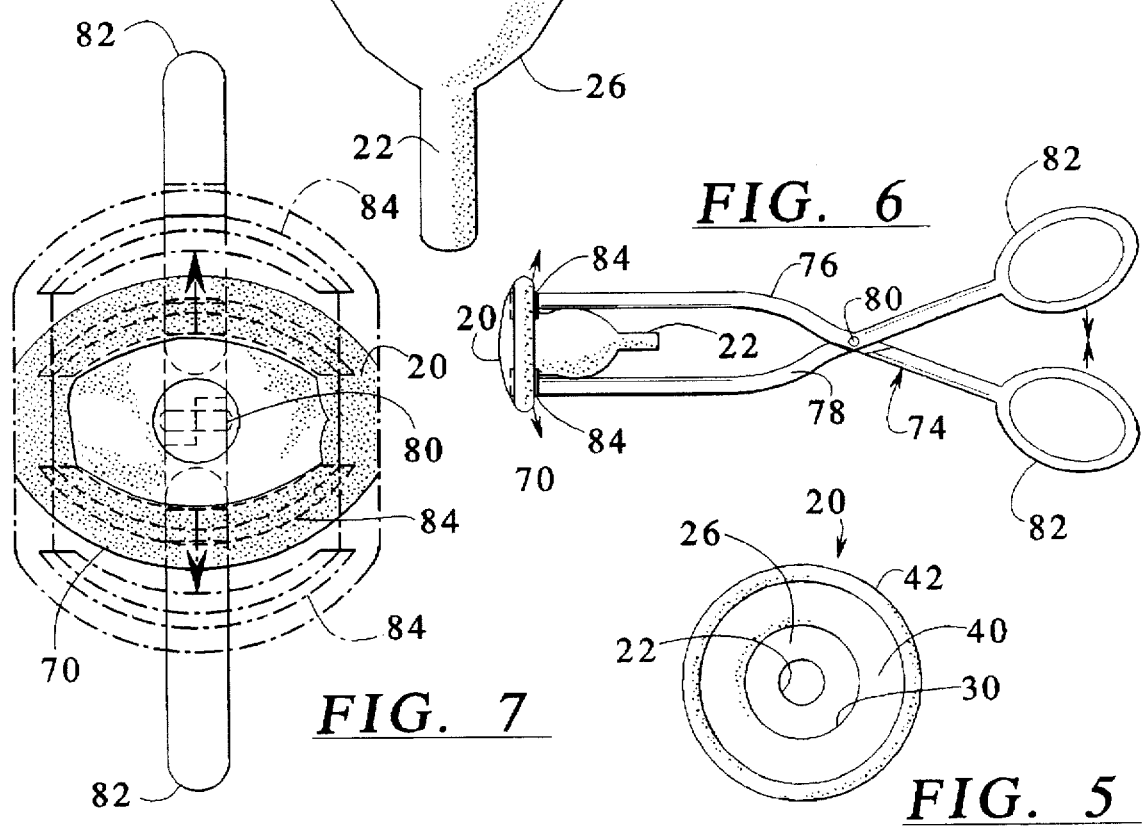
FIG. 6
FIG. 7
FIG. 5

EXTERNAL MALE CATHETER

BACKGROUND OF THE INVENTION

1. Field of the Invention

The present invention relates generally to a male urinary catheter and, in particular, to an external condom-type catheter.

2. Description of the Related Art

Urinary catheters are often required for a variety of circumstances including individuals undergoing medical treatment or surgery, individuals who are neurologically impaired and those who are bed ridden. Elderly individuals who are incontinent of urine may also require urinary catheters, and such catheters are frequently used in a nursing home environment. Such individuals may be required to wear internal catheters. Men who are incontinent of urine, either due to illness, trauma or medical treatment, may be able to wear an external catheter. External catheters are also used by men with normal urinary control, such as long distance drivers or aircraft pilots, who are forced by circumstances to be away from restroom facilities for extended periods of time.

Internal catheters are well known. They comprise a tube that is inserted into bladder through the urethra; the other end of the tube connects to a collection receptacle, such as a urine collection bag. Internal catheters may cause the patient discomfort and are associated with multiple side effects including urinary tract infection, bladder stones, bleeding, and increased risk of bladder cancer. However, internal catheters generally are not subject to leaking. External catheters for male individuals are generally in the form a sheath that is worn over the penis, the distal end of the sheath being connected to a tube that leads to a collection receptacle. Such external catheters are known as condom catheters due to their resemblance to condoms. External male catheters are prone to several problems, including leakage, becoming dislodged or pulled loose, or irritation and ulceration of the penile skin. For example, a male typically experiences nocturnal erections or changes in body position which tend to dislodge the external catheter from the proper position so that leakage occurs. One method to prevent the catheter from becoming dislodged is the use of a double-sided adhesive tape. To prevent the catheter from becoming dislodged, the double-sided adhesive tape is wrapped around the penis and the catheter is adhered to the tape. The tape does not stretch during the nocturnal erections, however, and so proves to be a considerable discomfort to the wearer or may constrict and injure the underlying tissues. Also, removal of the catheter from the tape and subsequent removal of the tape from the penis causes irritation to the skin of the penis and discomfort to the wearer. Condom catheters have also been designed with an adhesive on the sheath of the catheter or applied as a paint directly to the penis with similar attendant problems as mentioned above.

The known condom catheters are rolled much like a condom. When in place, the proximal end of the catheter may still be somewhat rolled, is adjacent the body and is snug about the penis. Removal is accomplished by grasping the proximal end and pulling away from the body to invert the catheter. During removal, especially during removal by someone other than the wearer such as medical personnel or caretakers, the skin of the penis and body hairs may inadvertently be pinched while trying to grasp the proximal end that is snugly against the penis. Also, body hairs may become caught in the rolled portion during normal wear and pulled during the removal process.

In the known external male catheters, the collection bag is worn on the leg generally in the region of the calf or thigh. Alternately, the collection bag is supported on a bed frame or bedside support during bed rest or for bed ridden patients. A tube connects the collection bag to the catheter.

SUMMARY OF THE INVENTION

The present invention provides an external male catheter which resists leakage and which stays in place during use. The present catheter also accommodates changes in diameter and length of the penis such as occur during erections without the catheter becoming dislodged. Additionally, the present catheter facilitates easy removal without pinching or pulling and with little or no discomfort. An applicator is also provided to assist wearers and health care workers in installing the present catheter.

Yet another embodiment of the invention provides an applicator built in to the external catheter.

In all embodiments of the invention, the external catheter prevents excessive pressure on the penis while the catheter is worn, and is safe from a vascular constriction standpoint so that tissue injury is avoided.

These and other objects and advantages of the invention are provided by an external male catheter that is an elastic sheath having, in order from distal to proximal end, a drain tube connection end for connection to a tube that leads to a collecting reservoir, a larger tubular portion of a diameter generally greater than the distal portion of the penis, a central portion of a lesser diameter than the larger tubular portion, and a cuff portion that is of a greater diameter than the central portion. These are formed together as a sheath sized to fit the human penis. The device may be formed initially in one piece or may be formed of a plurality of parts joined to one another.

The drain tube connection end is a tube that fits over a connector at the end of the collecting tube and that is removably affixed there in such a way that urine may flow from the catheter into the collecting tube. The drain tube connection end is preferably of a wall thickness sufficient to resist tearing or excessive stretching so as to stay in place on the connector. The connector may be of a slight conical shape or a stepped shape of increasing diameter over which the drain tube connection end is placed. Although usually not necessary, it is contemplated to use a band clamp or similar fastener to hold the external catheter to the end of the collecting tube. The collecting tube feeds into a collecting bag or the like which may be attached to the leg of the wearer or to a bed-side support. An alternate embodiment of the present invention provides a collecting bag at the upper leg of the wearer.

The transition between the large tubular portion and the drain tube connection end is accomplished by a generally hemispherical or conical portion. The drain tube connection end and the hemispherical or conical transition portion may be thicker than the rest of the device. An alternate embodiment provides a rigid portion at the distal end of the external catheter. The large tubular portion is of a diameter that is preferably greater than the largest diameter of the penis. The large tubular portion is preferably at least twice as long as the diameter of the large tubular portion. The large tubular portion is formed by a thin wall of the elastic material or by a rigid portion or may include a rigid ring.

Continuing in the proximal direction, the reduced diameter portion is of smaller diameter than the large tubular portion and is connected to the large tubular portion by a short transitional section having an external radius and an internal radius. The reduced diameter portion is provided in different sizes for different users and is of a diameter that is less than the diameter of the flaccid penis but no smaller than slightly less than the diameter of the manually extended flaccid penis. This provides a liquid tight seal between the device and the skin of the penis without cutting off circulation and nerve impulses and without requiring adhesives. By manually extended flaccid penis, what is meant here is the penis in its flaccid state which has been grasped at the end and pulled gently outward from the body. In this state, the shaft of the penis stretches to a smaller diameter than in the non-extended flaccid state. This diameter or slightly less is considered the smallest safe diameter for the reduced diameter portion. The reduced diameter portion is preferably approximately one and a half times its diameter in length in one embodiment.

The cuff portion is optionally provided and is connected to the reduced diameter portion by a short transition portion that includes an internal and an external radius. The cuff portion is larger in diameter than the reduced diameter portion and may be of approximately the same diameter as the larger tubular portion. The cuff portion is preferably shorter than the reduced diameter portion. The free end of the cuff portion may remain partially rolled, depending on the thickness of the material or on user preference. In one embodiment, the cuff unrolls completely when worn. The cuff may be of the same thin elastic material as the reduced diameter portion of the catheter, or may be of a greater thickness or a different, for example, more rigid, material. When worn, the cuff portion is folded back on the reduced diameter portion. Due to the difference in diameter of the cuff portion relative to the reduced diameter portion, an annular space or clearance is present between the reduced diameter portion and the cuff portion. During removal of the device, the wearer or health care worker places the fingers or thumbs into this annular space, grips the outside of the cuff, and pulls distally to remove the device. The elastic body of the device folds back on itself during such removal so that the device is peeled off the penis without requiring sliding movement of the device on and attendant irritation of the skin of the penis. The device is thus removed safely and comfortably. A small quantity of soap and water may be used at this time to facilitate removal, if desired.

The cuff provides an added advantage in that the end of the cuff, which may be rolled, is in a position away from the body when worn. Body hairs are not caught in that the rolled portion and, thus not pulled while the device is worn and especially when the device is removed. Also, body hairs are not pulled by the health care worker when removing the device, since the cuff provides a grip away from the body.

The cuff portion is not required in all embodiments of the present invention. Instead, the reduced diameter portion may be at the proximal end of the device. This embodiment of the device has a drain tube connection end, a first tubular portion of a large diameter and a second tubular portion of a small diameter. Such device stays in place during use without adhesives or tape and resists displacement by changes in size of the penis due to the relative diameter of the second tubular portion to the manually extended shaft of the penis.

Alternately, the present external catheter includes a cuff at an end opposite the drain tube connection end but the body of the device is a tubular portion of generally constant diameter. In other words, this embodiment is similar to the known external male catheters but with the addition of the cuff at the proximal end. The cuff is larger in diameter than the tubular body of the device so that a clearance between the body of the device and the cuff is present when the cuff is folded back on the body. This clearance provides room for gripping the end of the device for removal. The cuff provides the advantages of easy removal and avoiding catching and pulling of skin and body hair.

An alternate embodiment provides a conical, or funnel shaped, distal end portion of a relatively rigid material. The rigid end portion has a collecting tube connection end and a larger end to which the flexible tubular body of the present device is connected. The flexible tubular body to which the rigid material is attached has the reduced diameter portion as in the other embodiments and so stays in place.

An applicator may be included in the flexible tubular body of the present external catheter. In particular, a rigid ring may be provided inside the flexible larger tubular portion. The flexible tubular body of the present catheter is stretched over the ring so that the ring is within the larger distal portion of the catheter. The rigid ring supports the rolled catheter during shipping and storage and the ring provides a convenient grip location as the catheter is unrolled onto the penis. When the catheter is in place, the ring prevents the large diameter tubular portion from collapsing, such as from the reduced pressure caused by the column of liquid in the drain tube during urination. Another possibility provides a rigid ring in the cuff.

A further possibility is that the drain tube is eliminated and the collection bag is attached directly to the enlarged diameter distal portion of the catheter.

BRIEF DESCRIPTION OF THE DRAWINGS

FIG. 3 is a plan view of the device of the present invention as it is being removed;

FIG. 4 is a perspective view of the present device in a rolled condition prior to use;

FIG. 5 is an end view of the device of FIG. 1;

FIG. 6 is a side elevational view of an applicator device for aiding in putting the external catheter onto a wearer's penis.

FIG. 9 is a side elevational view of an embodiment of the present invention having a rigid distal end;

DETAILED DESCRIPTION OF THE PREFERRED EMBODIMENTS

Figure 1:
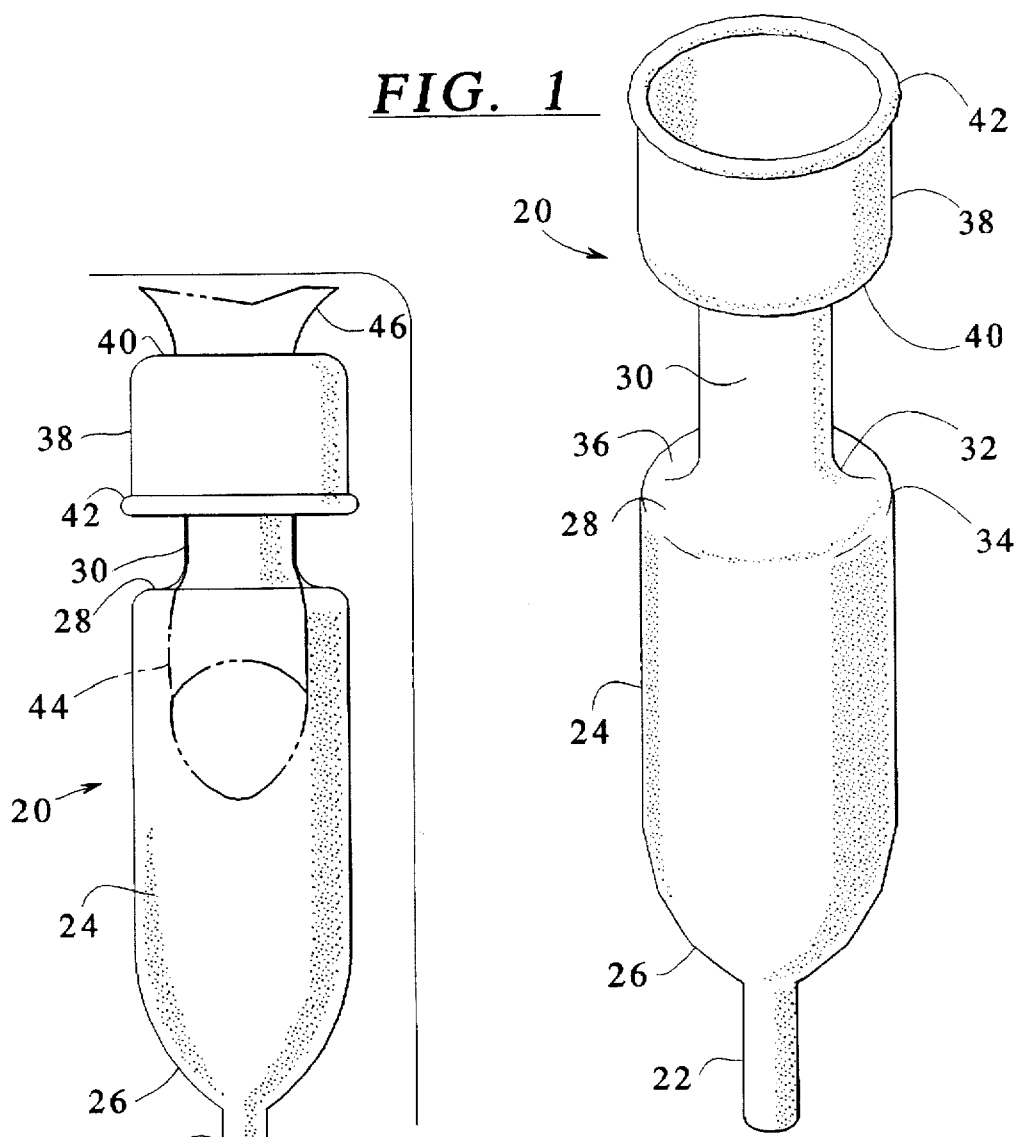
FIG. 1 is a side perspective view of the external male catheter according to the principles of the present invention.
Figure 2:
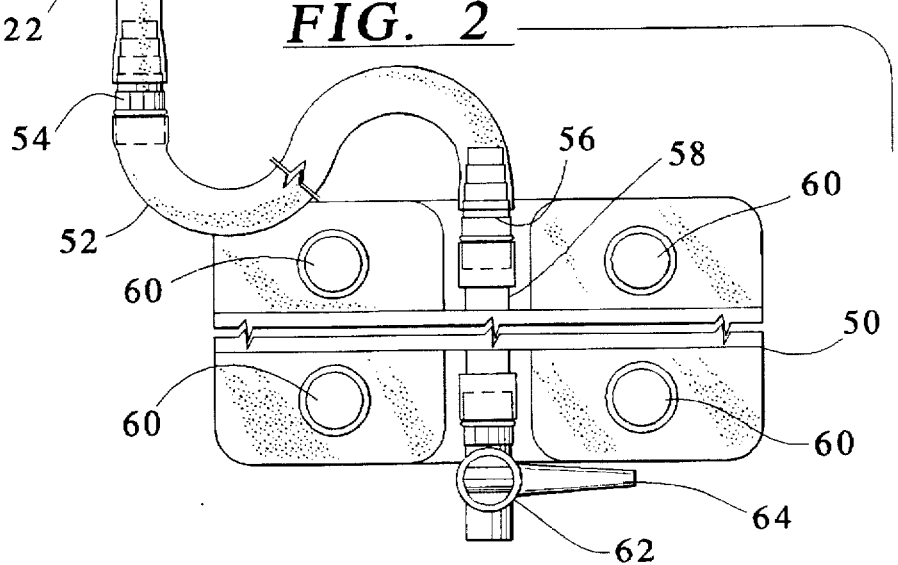
FIG. 2 is a plan view of the device of FIG. 1 in position while being worn, including a collection tube connected thereto and a collection bag on the opposite end of the collection tube.

Referring first to FIG. 1, an external male catheter 20 of the present invention is of an elastic material, such as latex, and includes a drain tube connection end 22 to which a drain tube, or collection tube, of a urine collecting system, as shown in FIG. 2, may be attached. The drain tube connection end 22 is hollow and is of an inside diameter to fit over an end of the drain tube in liquid tight engagement. The drain tube connection portion 22 is connected to a first tubular portion 24 that is of a greater diameter than the drain tube connection portion 22. A first transition portion 26 between the drain tube connection portion 22 and the first tubular portion 24 is generally hemispherical in shape, although it may be conical in shape or some other shape. Preferably, at least the drain tube connection portion 22 and possibly the transition portion 26 are formed of a relatively thick wall of the elastic material. The 24 is diameter first tubular portion 24 is generally of a thinner wall of the elastic material relative to the drain tube connection portion 22 so that the tubular portion 24 may stretch as necessary, although this need not always be the case since the length and diameter of the tubular portion 24 may be sufficient so that no stretching thereof is necessary. The thickened wall for the drain tube connection portion 22 and the transition portion 26 provides strength and resistance to stretching or tearing so that the device remains connected to the drain tube in use. As indicated, the tubular portion 24 may be of the same wall thickness as the drain tube connection portion 22.

The first tubular portion 24 is connected at an opposite end to a second transition portion 28 which provides a transition in diameter to a reduced diameter portion 30. The second transition portion 28 is formed by an inside radius 32 and an outside radius 34 and a short, flat tangential section 36. In the first preferred embodiment as illustrated, the radii 32 and 34 are 90 degree radii. Alternately, the radii may be less than 90 degrees. Also, the radii may merge so that no flat tangential section is present.

The reduced diameter portion 30 is connected to a cuff 38 by a third transition section 40. The cuff 38 is larger in diameter than the reduced diameter portion 30. The cuff 38 may be larger, smaller or of the same diameter as the first tubular portion 24, although the cuff 38 is preferably larger in diameter than the first tubular portion. The transition portion 40, like the transition portion 28, is formed of two radii and possibly a flat tangential portion. The cuff 38 of the illustrated embodiment ends in a roll 42 like a condom. Alternately, the cuff 42 may be completely unrolled. The cuff 38 is preferably shorter than the reduced diameter portion 30 so that a space in a longitudinal direction is present between the free end of the cuff 38 and the first tubular portion 24 when the cuff 38 is folded over as shown in FIG. 2.

Referring now to FIG. 2, the external catheter 20 of FIG. 1 is shown being worn on a human penis 44. The reduced diameter portion 30 snugly engages the shaft of the penis 44 while the first tubular portion 24 encloses the glans of the penis 44. The cuff 38 is adjacent the body 46 of the wearer. As illustrated in FIG. 2, the cuff 38 is folded back on the reduced diameter portion 30 when worn. By folding back the cuff 38, the roll 42 at the end of the cuff 30 is kept away from the body 46 so that it is less likely to catch body hairs. In addition, the cuff 38 provides a convenient grip for grasping and removing the present external catheter 20 from the wearer.

The external catheter 20 of the present invention provides a means for collecting urine from the human male. Accordingly, the catheter 20 is connected to a collection bag 50 by a drain tube 52. In particular, the drain tube 52 has a fitting 54 at the proximal end onto which the drain tube connection portion 22 is pushed. The fitting 54 has an outside surface of stepped increasing diameter than it pushed into the end of the drain connection portion 22 so that a liquid tight seal is formed. A similar stepped increasing diameter fitting 56 is provided at an intake 58 of the collecting bag 50 onto which the drain tube 52 is pushed in liquid-tight engagement. As is known, the collecting bag 50 has a one-way flow control valve (not shown) at the intake 58. Fasteners 60 are provided at the corners of the collecting bag 50 by which the collecting bag is supported, such as by leg straps (not shown) that encircle the leg of the wearer and support the bag 50. Alternately, the fasteners 60 may be affixed to an inside of a flight suit or space suit or they may be connected to a support, such as a bed-side support. A drain valve 62 with a valve opening lever 64 is provided at the lower end of the collecting bag 50.

The dimensions of the present catheter 20 are important for a liquid tight fit without discomfort or injury. In particular, the reduced diameter portion 30 is preferably to be substantially the same diameter as or slightly less than the shaft of the manually extended non-erect penis. The human penis when in a non-erect and relaxed state has a diameter of the shaft that will be referred to hereafter as the relaxed diameter. When the non-erect penis is grasped near the end and pulled outward from the body, without causing pain or discomfort to the individual, the shaft of the penis becomes of a smaller diameter than the relaxed diameter, this smaller diameter being referred to hereinafter as the manually extended non-erect diameter. The elongation necessary to determine the manually extended non-erect diameter may be performed without injury or discomfort, since the penis naturally becomes elongated during erections. A liquid tight seal is provided when the diameter of the reduced diameter portion 30 is in a range between the relaxed diameter to slightly less than the manually extended non-erect diameter. In this range, the shaft of the penis pushes outward on the reduced diameter portion 30 to form a liquid tight seal. The liquid tight seal is provided by the tendency of the penis to become shorter and thicker when released from the manually extended state. If the diameter of the reduced diameter portion 30 is larger than the relaxed diameter, leakage will occur, particularly when the penis is in the non-erect state. If the diameter of the reduced diameter portion 30 is substantially smaller than the manually extended non-erect diameter, then injury may occur as the result, for example, of blood flow possibly being reduced locally to the shaft skin as well as the blood flow to the distal end of the penis being reduced or cut off. In the present invention, the pressure on the penis is limited to a safe level, thus the invention is a substantial improvement over the previous devices.

Tests conducted by multiple volunteers confirm that thoughtful selection of the proper size of the device is essential to its successful use. A device which has a reduced portion which is larger than the manually extended dimension of the penis may readily slip off and fail quickly. A device which is substantially the same dimension as the extended penis will perform properly. A device which is substantially smaller may constrict the glans portion of the penis which leads to discomfort and possible failure. The tests confirm that the relationship between the size of the wearer's penis and the size of the device is critical for the successful utilization of the device and not by the shape alone.

The first tubular portion 24 is to be of a diameter larger than the reduced diameter portion 30. The glans of the penis is generally of a larger diameter than the shaft of the penis and the first tubular portion 24 is generally as large as or larger than the diameter of the glans. The first tubular portion 24 is preferably longer than its diameter and in a preferred embodiment is twice its diameter. The first tubular portion 24 may be of a length from 1.5 to five or six times its diameter, depending on the penal size of the wearer. The distal end of the penis may move freely in the first tubular portion 24 and the penis may even become erect, such as during a nocturnal erection, without dislocating the reduced diameter portion from its position on the shaft of the penis. Urination, whether under conscious control such as by a pilot, long distance driver, or astronaut, or not, such as by an individual who is incontinent of urine, likewise does not dislocate the reduced diameter portion 30. Urine is carried via the present catheter 20 and via the drain tube 52 to the collection bag 50. Any surge in the flow, such as from the start up of the urine flow, is accommodated by stretching of the first tubular portion 24 without dislodging the reduced diameter portion 30.

The shape of the present external catheter 20 may be the result of spray molding, injection molding or dipping a shaped mandrel. While the material from which the device 20 is formed may be constant, it is also contemplated to form some portions of different thicknesses. The reduced diameter portion 30 may be formed to be thicker than the body of the device to resist stretching, or the reduced diameter portion may be of a different material having a different modulus of elasticity so as to resist stretching. A second layer of material may be added at the reduced diameter portion to provide reinforcement. The preferred method of manufacturing the present device 20 is to dip an appropriately shaped mandrel in a liquid latex bath then remove it for curing of the latex layer adhered thereto. The recess in the mandrel that forms the transition portion 28 may accumulate a little more of the material during formation of the device so that the transition portion 28 is resistant to stretching. In particular, the radii and flat portion of the transition portion 28 may be caused to hold a slightly greater thickness of the elastic material during formation of the device to provide the resistance to stretching. It is contemplated to form the mandrel so that the transition portions or the reduced diameter portions, or both, are thicker than the body of the device so as to resist stretching.

In FIG. 3, the external catheter of FIGS. 1 and 2 is being removed by gripping the cuff 38 between the thumb and fingers and pulling away from the wearer. The cuff 38 provides a convenient gripping location for removal by the wearer himself or by a health care worker. The cuff opening is located away from the body hairs of the wearer so that the hairs are less likely to be gripped and pulled as the catheter 20 is being removed. As the cuff 38 is pulled, the external catheter 20 folds back on itself without requiring that it be slid on the skin. Thus, no irritation results. Once removed, no adhesive or tape remains on the wearer's penis.

With reference to FIG. 4, the present external catheter 20 is provided to the user in a rolled condition as shown. The cuff 38, reduced diameter portion 30, and at least part of the first tubular portion 24 are rolled into a roll 70. The roll 70 is preferably formed at a diameter more nearly that of the larger diameter first tubular portion 24 than the reduced diameter portion 30, although some reduction in diameter is unavoidable. The roll 70 may be supported on a support ring that is of a diameter corresponding to the first tubular portion 24 to hold the roll 70 in a position to enable easy installation of the device. Such a support ring extends from the roll 70 toward the drain tube connection portion 22.

FIG. 5 shows a view into the present device 20, including the roll 42 at the end of the cuff 38, the transition portion 40 that leads to the reduced diameter portion 30 and the transition portion 26 that leads to the drain tube connection portion 22. The view of FIG. 5 shows the present device in its unrolled state.

Figure 7:
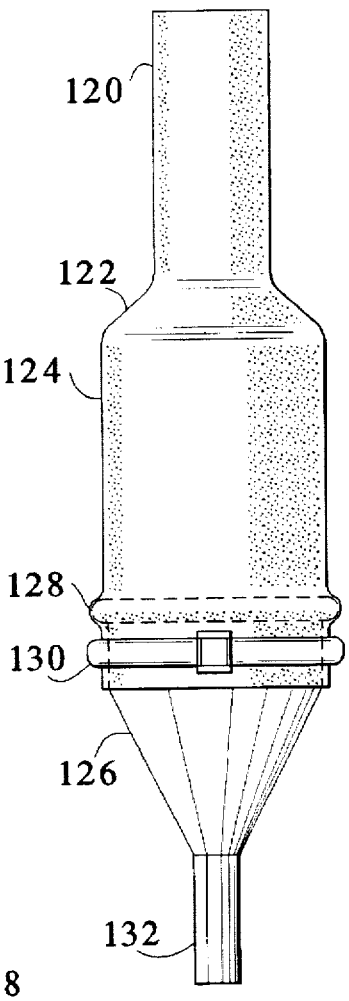
FIG. 7 is an end elevational view of the applicator of FIG. 6 showing the external catheter on the applicator of FIG. 6 and showing in broken outline the catheter in a stretched condition by the applicator for putting on the wearer.

Various applicators are contemplated for aiding the wearer or health care workers in putting the external catheter 20 onto the wearer's penis. One such applicator 74 is shown in FIGS. 6 and 7. The applicator 74 has two elements 76 and 78 connected by a pivot connection 80. The elements 76 and 78 do not cross at the pivot point 80 like a scissors or pliers, but pivot at the pivot point 80 like a clothes pin wherein the movement of handles 82 on the elements 76 and 78 toward one another, as indicated by the arrows, moves the working ends apart. The end of the applicator opposite the handles 82 includes a pair of arc members 84 having a channel into which the roll 70 fits when stretched thereon. The applicator is moved to the end of the penis and the handles 82 squeezed together to open the roll 70 of the device 20 so that the roll is moved over the glans of the penis. The present external catheter 20 is then unrolled from the arc members 84 into position on the penis. The illustrated applicator 74 permits the wearer to easily apply the external catheter himself, or a health care worker may apply the present device to a patient, all without excessive handling of the patient.

An alternate applicator has the arc members turned at a right angle relative to the arc members shown in FIGS. 6 and 7. This arrangement permits some wearers to more easily install the device, and may permit a bed-side health care worker to install the device more easily as well.

Figure 8:
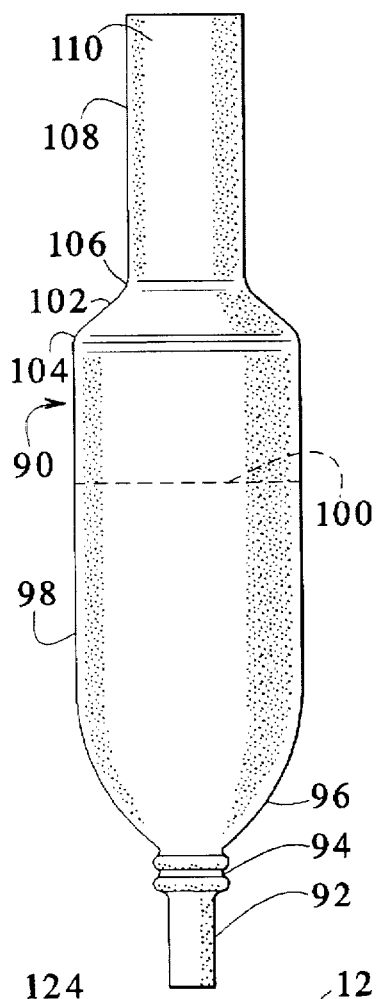
FIG. 8 is a side elevational view of another embodiment of the present invention without the cuff.

FIG. 8 shows an alternate embodiment of the present external catheter 90. This embodiment has a drain tube connection end 92 which has an accordion pleated end 94 adjacent the transition portion 96. The accordion pleats 94 permit the drain tube connection end 92 to flex relative to the transition portion 96 without pinching closed. The transition portion 96 leads to the first tubular portion 98 that is generally of a larger diameter than the glans of the wearer's penis. The material of the lower portion of the external catheter 90 below the line 100 is thicker than above the line 100. The first tubular portion need not flex since it is sized to accommodate any changes in size of the penis, and so this thicker portion has no detrimental effect on the operation of the external catheter.

A transition portion 102 connected to the first tubular portion 98 has a conical surface region with inside and outside radii 104 and 106. The radii 104 and 106 are less than 90 degrees, resulting in the conical surface instead of the flat transition surface of the previously described embodiment. The transition portion 102 is connected to a reduced diameter portion 108 which ends at a free end 110 without a cuff. The reduced diameter portion 108 in combination with the larger diameter portion 98 holds the external catheter 90 in place without adhesives or tape and without injury or discomfort to the wearer.

Figure 10:
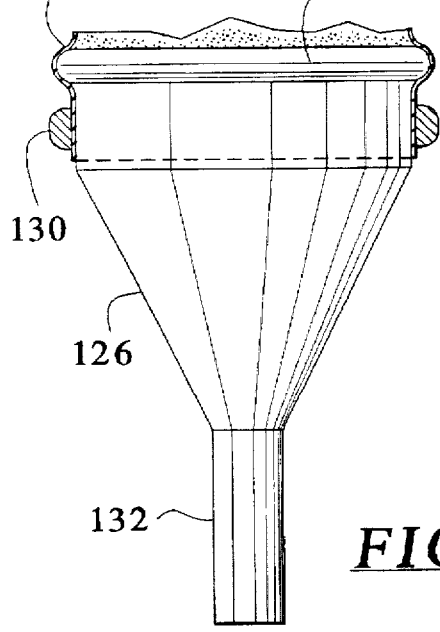
FIG. 10 is an enlarged view of the rigid end of the embodiment of FIG. 9.

A further embodiment is shown in FIGS. 9 and 10. This embodiment has the reduced diameter portion 120 connected to a transition portion 122 which leads to a first tubular portion 124, just as in the foregoing embodiments. However, the embodiment of FIGS. 9 and 10 includes a rigid end piece 126 that is of a funnel shape. A proximal end of the rigid piece 126 has a lip 128 over which the first tubular portion 124 is placed. The first tubular portion 124 is held in place by a band clamp 130 disposed distally from the lip 128. Other attachment means, such as adhesives, are also possible for affixing the rigid piece 126 to the first tubular portion 124. The rigid piece 126 has a drain tube connection end 132 like the other embodiments.

Figure 11:
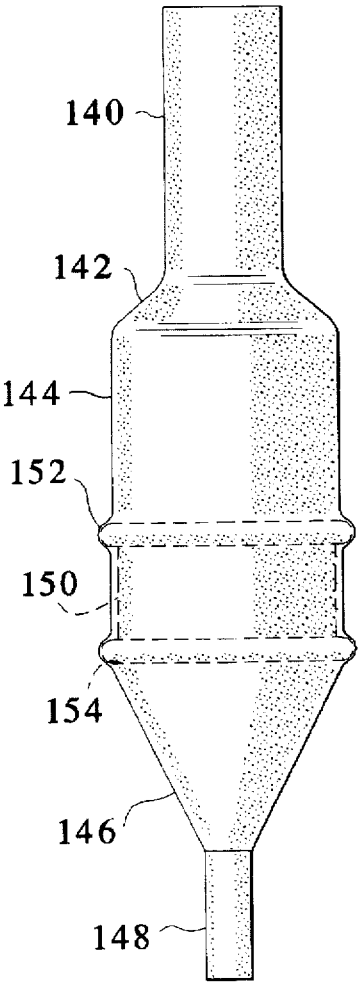
FIG. 11 is a side elevational view of an embodiment of the invention having a rigid ring within the distal portion of the device.
Figure 12:
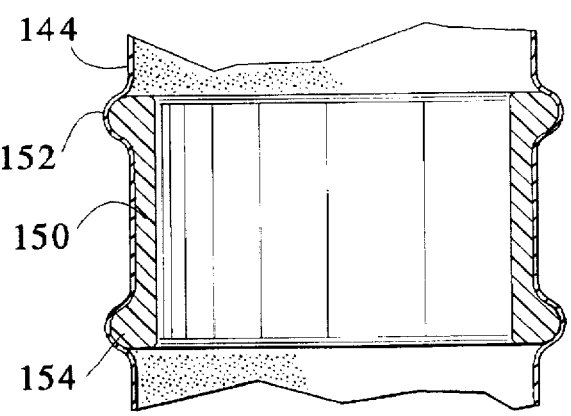
FIG. 12 is an enlarged cross section of the rigid ring of the embodiment of FIG. 11.

FIGS. 11 and 12 show an embodiment having the reduced diameter portion 140 connected to a transition portion 142 that connects to a first tubular portion 144 which in turn connects to a transition portion 146 to a drain tube connection portion 148. The transition portion 146 is conical in shape. This embodiment includes a rigid ring 150 disposed within the first tubular portion 144. The ring 150 has a raised lip 152 and 154 at each end and a smooth interior surface.

The rigid end piece 126 and the rigid ring 150 of the embodiments shown in FIGS. 9-12 serve several purposes. First, the portion of the external catheter disposed proximally from the ring 150 or end piece 126 may be rolled and stretched over the raised lip 152 and 128, respectively. Since the end piece 126 and the ring 150 are of a diameter corresponding approximately to the diameter of the first tubular portion, which in turn is larger than the diameter of the glans of the penis, the end piece 126 and the ring 150 each serve as applicators. The proximal portion of the device is in a stretched state when on the end piece 126 or the ring 150. By placing these rigid portions over the end of the penis and unrolling the proximal portion of the device onto the penis, the external catheter is installed without difficulty and without the use of an additional applicator.

Figure 13:
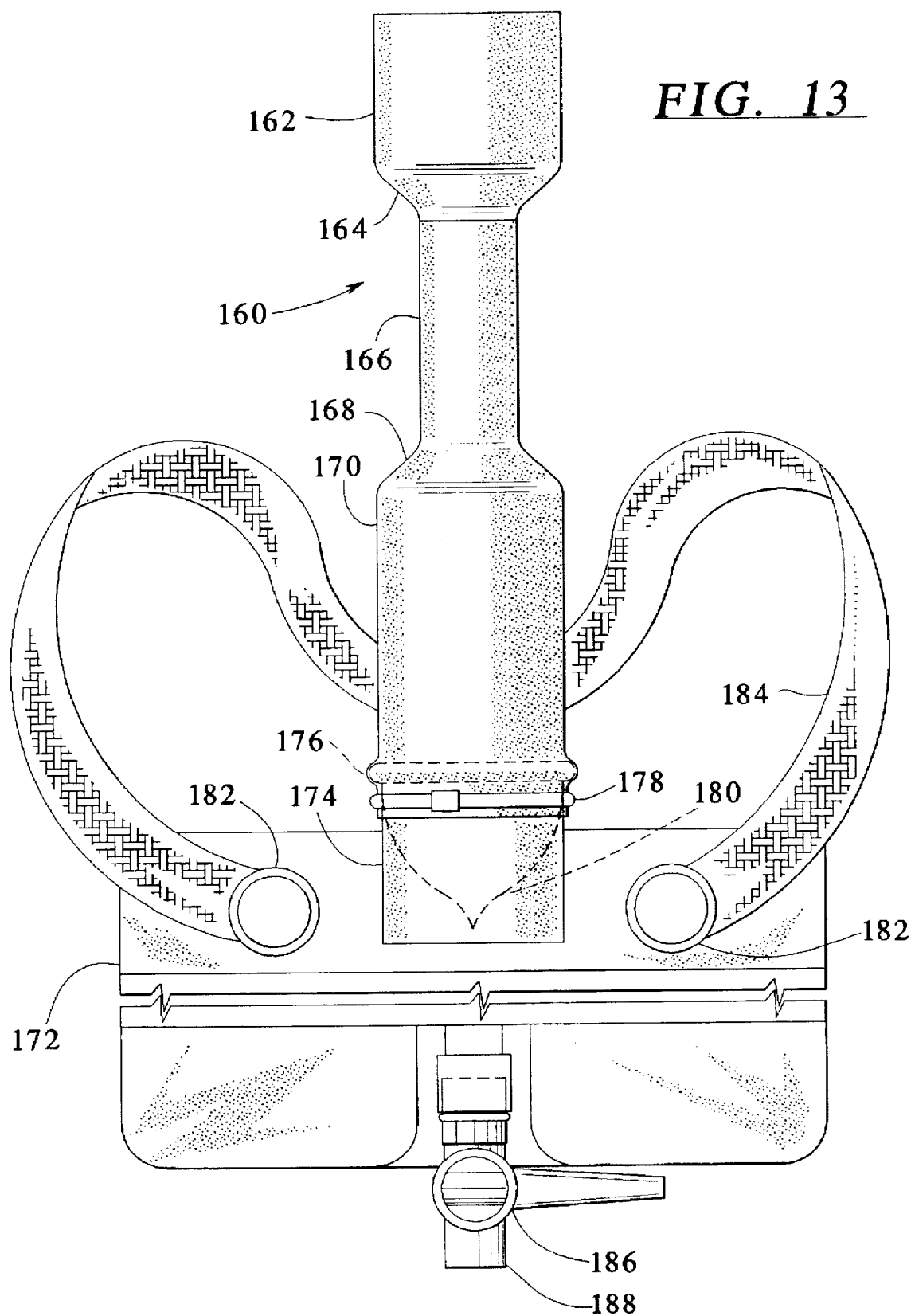
FIG. 13 is a side elevational view of another embodiment having a collecting bag attached to the distal end of the external catheter.

A further embodiment 160 is shown in FIG. 13, wherein the external catheter has a cuff 162 that connects to a transition portion 164 that connects to a reduced diameter portion 166 that connects to a transition portion 168 that in turn connects to a first tubular portion 170. Instead of a drain tube connection portion, however, the present embodiment has a direct connection to a collecting bag 172 by a connection ring 174. The connection ring 174 serves as the intake for the collection bag 172 and has a raised lip 176 over with the first tubular portion 170 is stretched. A band clamp 178 or other fastening means is provided to connect the first tubular portion 170 to the connection ring 174. The collecting bag 172 has a valve 180, such as a flutter valve, at the intake in the connection ring 174 to prevent back-flow of the urine collected in the collection bag 172.

The collection bag 172 includes connectors 182 to which a leg strap 184 is attached. The leg strap 184 encircles the wearer's thigh, although it is otherwise similar to the leg strap for encircling the wearer's calf as used with the collection bag 50 of FIG. 2. A drain valve 186 for a drain 188 is provided at the lower end of the collection bag 172.

When used, the present device is initially in a rolled state and is placed adjacent the end of the penis whereupon it is unrolled over the penis, such as the manually extended penis, until the small diameter central portion is extended along the shaft of the penis. For embodiments having a cuff, the cuff end may be folded back over the central portion or it may move to the folded position on its own as the result of contact with the body. The connector on the end of the drain tube it inserted into the end of the drain connection portion. Wetting the connector before insertion into the drain connection portion may aid the insertion.

Thereafter, as with the known devices, the drain tube is connected to the fitting at the top of the collection bag and the collection bag is strapped to the wearer's leg. The urine collecting system may be worn under street clothes for individuals who are incontinent of urine or long distance drivers or the like, or it may be worn under flight suits of pilots or astronauts. If the individual is bed-ridden, such as in a hospital or nursing home, the collecting bag need not be strapped to the wearer's leg but may be affixed to a support.

A contemplated improvement for the present invention is to form the catheter in one piece with the drain tube.

The present device provides a level of comfort and security not found in known external catheters. It resists inadvertent removal without adhesives and yet is easily removed when desired.

The size of the present catheter relative to the penis of the wearer, and particularly the size of the reduced diameter portion relative to the shaft diameter of the penis, is fundamental in the operation of the present catheter. For instance, it is recommended that the diameter of the reduced diameter portion match as closely as possible to the diameter of the flaccid, manually extended penis. Testing has found that catheters having a reduced diameter portion which is larger than the manually extended diameter may have a greater tendency to leak or come loose than catheters which are the same size or slightly smaller than the manually extended diameter. The reduced diameter portion should preferably be at least as small as the diameter of the flaccid, non-extended penis.

It is contemplated to offer the present catheter in a range of sizes to fit the full range of human penis sizes. For instance, one study found a range of diameters from 16 mm to 44 mm for flaccid, non-extended penises. Mean diameters for the study group were in a range from 21 to 37 mm. A greater range is possible as the scope of the study was somewhat limited. A study also found that the circumference of the flaccid penis is reduced in a range of 0 to 24 percent when the penis is stretched. An average change in penis circumference for the study group is 7 to 17 percent decrease when the flaccid penis is manually extended. It is contemplated to accommodate these ranges and perhaps greater ranges with the apparatus of the present invention.

Although other modifications and changes may be suggested by those skilled in the art, it is the intention of the inventor to embody within the patent warranted hereon all changes and modifications as reasonably and properly come within the scope of his contribution to the art.

I claim:

1. An external male urinary catheter and applicator, comprising:

a drain tube connecting portion;

a first tubular portion connected to said drain tube connecting portion, said first tubular portion being of a first diameter greater than a glans of a human penis, said first tubular portion being of a length approximately twice said first diameter;

a second tubular portion connected to said first tubular portion at an end of said first tubular portion opposite said drain connecting portion, said second tubular portion of a second diameter less than said first diameter, said second diameter being substantially equal to a diameter of a manually extended shaft of the human penis;

a third tubular portion connected to an end of said second tubular portion opposite said first tubular portion, said third tubular portion being of a third diameter greater than said second diameter;

said first and second and third tubular portions forming a sheath for wearing on the human penis with said first tubular portion at a distal position and said third tubular portion at a proximal position;

an applicator having first and second curved channels onto which at least said second and third tubular portions are positioned when in a rolled condition; and means for moving said first and second curved channels apart when said second and third tubular portions are placed thereon in a rolled condition to facilitate donning of said external catheter.

2. An external male urinary catheter and applicator as claimed in claim 1, wherein said means for moving comprises a pivot-connected pair of arms which are manually operable to move said first and second curved channels apart.

* * * * *